US00PP13828P29

(12) United States Plant Patent
Kobayashi

(10) Patent No.: US PP13,828 P2
(45) Date of Patent: May 20, 2003

(54) POINSETTIA PLANT NAMED 'ECKALCOTT'

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/087,968

(22) Filed: Mar. 4, 2002

(51) Int. Cl.[7] ..... A01H 5/00
(52) U.S. Cl. ..... Plt./307
(58) Field of Search ..... Plt./307, 303

*Primary Examiner*—Bruce R. Campell
*Assistant Examiner*—June Hwu
(74) *Attorney, Agent, or Firm*—C. A. Whealy

(57) ABSTRACT

A new and distinct cultivar of Poinsettia plant named 'Eckalcott', characterized by its inflorescences with dark red-colored flower bracts with irregularly incised margins; dark green-colored leaves with irregularly incised margins; uniform and mounded plant habit; early flowering habit; multiple nectaries per cyathium; and excellent post-production longevity.

2 Drawing Sheets

BOTANICAL CLASSIFICATION/CULTIVAR DESIGNATION

*Euphorbia pulcherrima* Willd. cultivar Eckalcott.

BACKGROUND OF THE INVENTION

The present Invention relates to a new and distinct cultivar of Poinsettia plant, botanically known as *Euphorbia pulcherrima* Willd., and hereinafter referred to by the name 'Eckalcott'.

The new Poinsettia a product of a induced mutation breeding program conducted by the Inventor in Encinitas, Calif. The objective of the breeding program is to create new Poinsettia cultivars having flower bracts with desirable colors, uniform plant habit and excellent post-production longevity.

The new Poinsettia is an induced mutation of the *Euphorbia pulcherrima* Willd. cultivar Bright Red Freedom, disclosed in U.S. Plant Pat. No. 10,572. Mutations were induced by exposing unrooted cuttings of 'Bright Red Freedom' to gamma radiation. The new Poinsettia was discovered and selected by the Inventor as a single flowering plant within a population of irradiated plants of the cultivar Bright Red Freedom in December, 1999, in a controlled environment in Encinitas, Calif. The selection of this plant was based on its dark red-colored flower bracts with irregularly incised margins.

Asexual reproduction of the new Poinsettia by terminal cuttings propagated in a controlled environment in Encinitas, Calif., since January, 2000, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckalcott'. These characteristics in combination distinguish 'Eckalcott' as a new and distinct cultivar:

1. Inflorescences with dark red-colored flower bracts with irregularly incised margins.

2. Dark green-colored leaves with irregularly incised margins.

3. Uniform and mounded plant habit.

4. Early flowering; natural season flower maturity date is late November to early December for plants grown in Encinitas, Calif.; response time, about 9 weeks.

5. Multiple nectaries per cyathium.

6. Excellent post-production longevity.

Plants of the new Poinsettia are most similar to plants of the parent, the cultivar Freedom Bright Red. In side-by-side comparisons conducted in Encinitas, Calif., plants of the new Poinsettia had darker red-colored bracts and flowered about 10 days later than plants of the cultivar Freedom Bright Red. In addition, plants of the new Poinsettia had incised leaf and flower bract margins whereas plants of the cultivar Freedom Bright Red did not have incised leaf and flower bract margins.

Plants of the new Poinsettia differ primarily from plants of the cultivar Eckalain, disclosed in a U.S. Plant Patent application filed concurrently, in flower bract coloration.

Plants of the new Poinsettia can also be compared to plants of the cultivar Eckada, disclosed in U.S. Plant Pat. No. 11,124. In side-by-side comparisons conducted in Encinitas, Calif., plants of the new Poinsettia had darker red-colored bracts than plants of the cultivar Eckada. In addition, plants of the new Poinsettia had incised leaf and flower bract margins whereas plants of the cultivar Eckada did not have incised leaf and flower bract margins.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of a typical flowering plant of 'Eckalcott' grown in a 16.5-cm container.

The photograph at the top of the second sheet comprises a top perspective view of a typical flowering plant of 'Eckalcott'.

The photograph at the bottom of the second sheet comprises a close-up view of typical leaves and flower bracts of 'Eckalcott' (left) and 'Eckada' (right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the autumn and winter under commercial practice in a polycarbonate-covered greenhouse with day temperatures about 24 to 29° C., night temperatures about 19° C., and light levels about 4,000 foot-candles. Single plants were grown in 16.5-cm pots and pinched once. Plants were flowered under natural season short day/long night conditions. Plants were about 18 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Eckalcott.

Parentage: Induced mutation of *Euphorbia pulcherrima* Willd. cultivar Bright Red Freedom, disclosed in U.S. Plant Pat. No. 10,572.

Propagation:

*Type cutting.*—Terminal cuttings.

*Time to initiate roots.*—About 10 days at 20 to 22° C.

*Time to develop roots.*—About 28 days at 24° C.

*Root description.*—Thick, fibrous and freely-branching.

Plant description:

*Plant form.*—Inverted triangle; top of plant mounded.

*Growth habit.*—Upright and uniform plant habit. Moderately vigorous to vigorous.

*Plant height.*—About 29 cm.

*Plant diameter or spread.*—About 48 cm.

*Lateral branch description.*—Quantity: About seven lateral branches develop after pinching. Length: About 21 cm. Diameter: About 7 mm. Internode length: About 1.75 cm. Strength: Strong. Texture: Smooth; glabrous. Color: 146A overlain with 59A.

*Foliage description.*—Arrangement: Alternate, single. Quantity of leaves per lateral branch: About eight. Length: About 10.8 cm. Width: About 7.5 cm. Shape: Elliptic. Apex: Acuminate. Base: Obtuse with truncate tendencies. Margin: Irregularly incised. Venation pattern: Pinnate. Texture: Upper surface: Glabrous. Lower surface: Slightly pubescent. Surface: Slightly rugose. Aspect: Mostly flat. Orientation: Mostly horizontal. Color: Young foliage, upper surface: Darker than 146A. Young foliage, lower surface: 146A. Fully expanded foliage, upper surface: Darker than 147A. Fully expanded foliage, lower surface: 147A. Venation: Upper surface: 147B. Lower surface: Lighter than 181D. Petiole: Length: About 2.7 cm. Diameter: About 2.5 mm. Texture, upper and lower surfaces: Smooth; glabrous. Color: 46A.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Early flowering, response time, about 9 weeks; natural season flower maturity date is late November to early December for plants grown in Encinitas, Calif.

*Post-production longevity.*—Plants of the new Poinsettia maintain good substance and bract color for about four weeks under interior conditions.

*Inflorescence size.*—Diameter: About 28 cm. Height (depth): About 4 cm.

*Flower bracts.*—Quantity per inflorescence: About 22. Length, largest bracts: About 12.5 cm. Width, largest bracts: About 10.4 cm. Shape: Elliptic. Apex: Acuminate. Base: Obtuse with truncate tendencies. Margin: Irregularly incised. Texture, upper and lower surfaces: Glabrous; velvety. Surface: Rugose. Aspect: Mostly flat. Orientation: Mostly horizontal to slightly upright. Venation pattern: Pinnate. Color: Developing or transitional bracts, upper and lower surfaces: 53A. Fully developed bracts, upper surface: Brighter than 53B; color does not fade with subsequent development. Fully developed bracts, lower surface: 53B. Venation, upper and lower surfaces: Similar to flower bract color. Bract petiole: Length: About 1.1 cm. Diameter: About 2 mm. Texture, upper and lower surfaces: Smooth; glabrous. Color: 59A.

*Cyathia.*—Quantity per corymb: About 10. Diameter of cyathia cluster: About 2.5 by 3 cm. Length: About 8 mm. Width: About 7 mm. Shape: Ovoid. Color, immature and mature: 144A. Peduncle: Length: About 2 mm. Diameter: About 2 mm. Strength: Strong. Aspect: Mostly upright to slightly outward. Texture: Smooth; glabrous. Color: 144B. Stamens: Quantity per cyathium: At least 10. Anther shape: Oval. Anther length: Less than 1 mm. Anther color: 46A. Amount of pollen: None observed. Pistils: None observed. Nectaries: Quantity per cyathium: About five. Size: About 2 mm by 3 mm. Color: Apex, 31A; lateral surfaces, 43B.

Disease/pest resistance: Resistance to pathogens and pests common to Poinsettias has not been observed on plants grown under commercial conditions.

It is claimed:

1. A new and distinct cultivar of Poinsettia plant named 'Eckalcott', as illustrated and described.

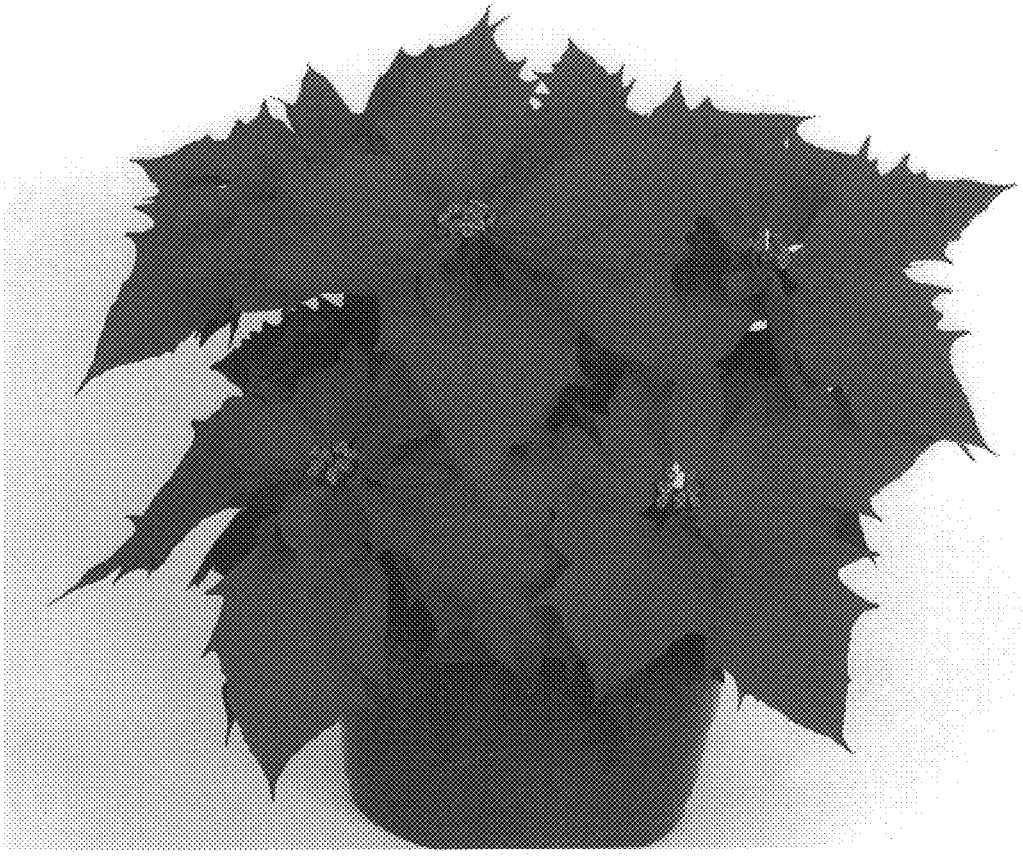

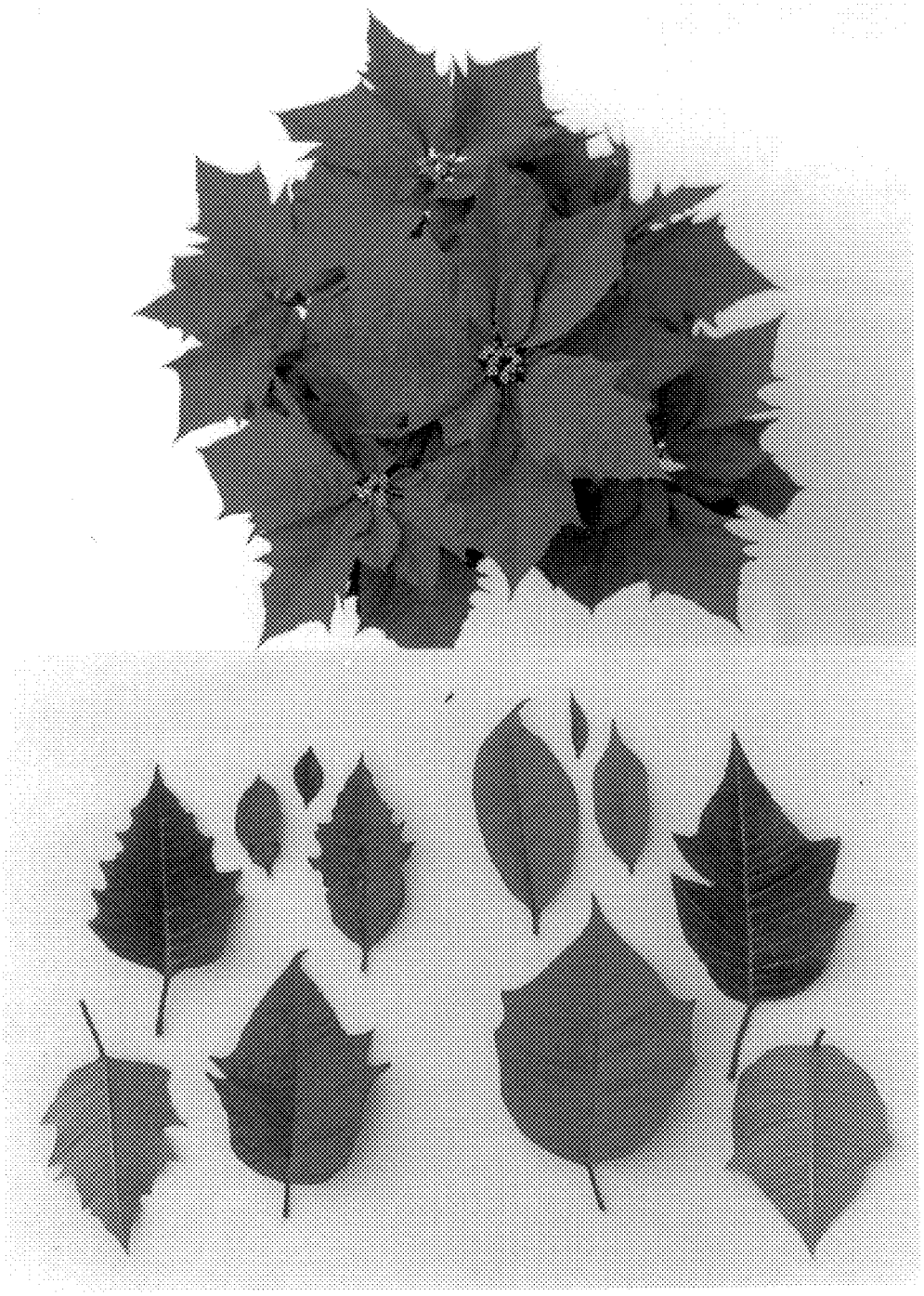

* * * * *